(12) United States Patent
Govari et al.

(10) Patent No.: US 7,201,749 B2
(45) Date of Patent: *Apr. 10, 2007

(54) EXTERNALLY-APPLIED HIGH INTENSITY FOCUSED ULTRASOUND (HIFU) FOR PULMONARY VEIN ISOLATION

(75) Inventors: Assaf Govari, Haifa (IL); Yitzhack Schwartz, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 438 days.

This patent is subject to a terminal disclaimer.

(21) Appl. No.: 10/370,134

(22) Filed: Feb. 19, 2003

(65) Prior Publication Data

US 2004/0162550 A1 Aug. 19, 2004

(51) Int. Cl.
  *A61B 18/18* (2006.01)
  *A61B 8/00* (2006.01)
(52) U.S. Cl. ............ 606/27; 606/41; 600/439
(58) Field of Classification Search ....... 600/424, 600/436–466; 601/2–4; 604/22; 128/898; 606/27–31, 41
See application file for complete search history.

(56) References Cited

U.S. PATENT DOCUMENTS

| | | | |
|---|---|---|---|
| 4,401,124 A | 8/1983 | Guess et al. | |
| 4,979,948 A | 12/1990 | Geddes et al. | |
| 5,092,336 A | 3/1992 | Fink | |
| 5,109,859 A | 5/1992 | Jenkins | |
| 5,242,438 A | 9/1993 | Saadatmanesh et al. | |
| 5,366,490 A | 11/1994 | Edwards et al. | |
| 5,391,199 A | 2/1995 | Ben-Haim | |
| 5,433,708 A | 7/1995 | Nichols et al. | |
| 5,590,657 A * | 1/1997 | Cain et al. ......... | 600/439 |
| 5,676,692 A * | 10/1997 | Sanghvi et al. ...... | 607/98 |
| 5,693,043 A | 12/1997 | Kittrell et al. | |
| 5,807,395 A | 9/1998 | Mulier et al. | |
| 5,840,025 A | 11/1998 | Ben-Haim | |
| 5,891,134 A | 4/1999 | Coble et al. | |
| 5,938,600 A | 8/1999 | Van Vaals et al. | |
| 5,971,983 A | 10/1999 | Lesh | |

(Continued)

FOREIGN PATENT DOCUMENTS

WO   WO 00/67656 A2   11/2000

(Continued)

OTHER PUBLICATIONS

Mickael Tanter, Jean-Louis Thomas and Mathias Fink, Focusing through skull with time reversal mirrors. Application to hyperthermia, Proc. IEEE 1996 Ultrason. Symposium, pp. 1289-1293.*

(Continued)

*Primary Examiner*—Michael Peffley
(74) *Attorney, Agent, or Firm*—Louis J. Capezzuto

(57) ABSTRACT

Apparatus is provided for performing ablation of cardiac tissue using ultrasound. The apparatus includes a beacon, adapted to be placed at a cardiac site in a body of a subject. The apparatus further includes a set of ultrasound transducers, each transducer adapted to detect a respective ultrasound signal coming from the beacon. Each transducer is adapted to output a time-reversed ultrasound signal, reversed in time with respect to a property of at least one of the beacon signals, and configured to ablate the cardiac tissue.

36 Claims, 2 Drawing Sheets

U.S. PATENT DOCUMENTS

| | | | |
|---|---|---|---|
| 6,004,269 | A | 12/1999 | Crowley et al. |
| 6,012,457 | A | 1/2000 | Lesh |
| 6,024,740 | A | 2/2000 | Lesh et al. |
| 6,053,909 | A | 4/2000 | Shadduck |
| 6,064,902 | A | 5/2000 | Haissaguerre et al. |
| 6,090,084 | A | 7/2000 | Hassett et al. |
| 6,117,101 | A | 9/2000 | Diederich et al. |
| 6,156,028 | A | 12/2000 | Prescott |
| 6,164,283 | A | 12/2000 | Lesh |
| 6,190,382 | B1 | 2/2001 | Ormsby et al. |
| 6,245,064 | B1 | 6/2001 | Lesh et al. |
| 6,251,109 | B1 | 6/2001 | Hassett et al. |
| 6,296,619 | B1 | 10/2001 | Brisken et al. |
| 6,447,448 | B1 * | 9/2002 | Ishikawa et al. ............ 600/300 |
| 6,632,223 | B1 | 10/2003 | Keane |
| 6,679,269 | B2 | 1/2004 | Swanson |
| 2001/0041880 | A1 | 11/2001 | Brisken et al. |
| 2002/0065512 | A1 | 5/2002 | Acker |
| 2003/0125726 | A1 | 7/2003 | Maguire et al. |
| 2003/0135112 | A1 * | 7/2003 | Ritter et al. ................ 600/424 |
| 2004/0059265 | A1 * | 3/2004 | Candy et al. .................. 601/2 |
| 2004/0162507 | A1 | 8/2004 | Govari |

FOREIGN PATENT DOCUMENTS

| | | |
|---|---|---|
| WO | WO 01/72373 A2 | 10/2001 |
| WO | WO 01/82778 A2 | 11/2001 |

OTHER PUBLICATIONS

Pappone C, Rosanio S, Oreto G, Tocchi M, Gugliotta F, Vicedomini G, Salvati A, Dicandia C, Mazzone P, Santinelli V, Gulletta S, Chierchia S, *Circumferential Radiofrequency Ablation of Pulmonary Vein Ostia: A New Anatomic Approach for Curing Atrial Fibrillation*, Circulation 102:2619-2628 (2000).

Natale A, Pisano E, Shewchik J, Bash D, Fanelli R. MD; Potenza D; Santarelli P; Schweikert R; White R; Saliba W; Kanagaratnam L; Tchou P; Lesh M, *First Human Experience With Pulmonary Vein Isolation Using a Through-the-Balloon Circumferential Ultrasound Ablation System for Recurrent Atrial Fibrillation*, Circulation 102:1879-1882 (2000).

Scheinman MM, Morady F. Nonpharmacological Approaches to Atrial Fibrillation. *Circulation* 2001;103:2120-2125.

Wang PJ, Homoud MK, Link MS, Estes III NA. Alternate energy sources for catheter ablation. *Curr Cardiol Rep* Jul. 1999;1 (2) :165-171.

Fried NM, Lardo AC, Berger RD, Calkins H, Halperin HR. Linear lesions in myocardium created by Nd:YAG laser using diffusing optical fibers: in vitro and in vivo results. *Lasers Surg Med* 2000;27(4) :295-304.

Keane D, Ruskin J, Linear atrial ablation with a diode laser and fiber optic catheter. *Circulation* 1999; 100:e59-e60.

Ware D, et al., Slow intramural heating with diffused laser light: A unique method for deep myocardial coagulation. *Circulation*; Mar. 30, 1999; pp. 1630-1636.

Christian Dorme et al. Ultrasonic Beam Steering Through Inhomogeneous Layers With a Time Reversal Mirror. IEEE Transactions on Ultrasonics, Ferroelectrics, and Frequency Control, vol. 43, No. 1, Jan. 1996.

M. Fink et al. Self Focusing in Inhomogeneous Media With "Time Reversal" Acoustic Mirrors. 1989 Ultrasonics Symposium—681.

Mathias Fink Time Reversal of Ultrasonic Fields—Part 1: Basic Principles. IEEE Transactions on Ultrasonics, Ferroelectrics, and Frequency Control, vol. 39, No. 5, Sep. 1992.

Mickaël Tanter et al. Focusing and Steering Through Absorbing and Aberrating Layers: Application to Ultrasonic Propagation Through the Skull. J. Acoust. Soc. Am 103 (5) Pt. 1, May 1998.

Mickaël Tanter et al. Focusing Through Skull With Time Reversal Mirrors. Application to Hyperthermia. 1996 IEEE Ultrasonics Symposium—1289.

Francois Wu et al. Time Reversal of Ultrasonic Fields—Part II: Experimental Results. IEEE Transactions on Ultrasonics, Ferroelectrics, and Frequency Control, vol. 39, No. 5, Sep. 1992.

Eigler NL et al., "Implantation and Recovery of Temporary Metallic Stents in Canine Coronary Arteries", J Am Coll Cardiol 1993;22(4)1207-1213.

Middleton JC et al., "Synthetic Biodegradable Polymers as Orthopedic Devices", Biomaterials 21 (2000) 2335-2346.

European Search Report EP03257414 dated Mar. 16, 2004.

European Search Report EP04250864 dated May 27, 2004.

* cited by examiner

EXTERNALLY-APPLIED HIGH INTENSITY FOCUSED ULTRASOUND (HIFU) FOR PULMONARY VEIN ISOLATION

CROSS-REFERENCES TO RELATED APPLICATIONS

This application is related by subject matter to U.S. patent application Ser. No. 10/370,381, entitled, "Externally-Applied High Intensity Focused Ultrasound (HIFU) For Therapeutic Treatment," filed on Aug. 19, 2003, which is assigned to the assignee of the present patent application and is incorporated herein by reference.

FIELD OF THE INVENTION

The present invention relates generally to use of ultrasound in medical technology applications, and specifically to methods and apparatus for performing pulmonary vein isolation using high-intensity focused ultrasound (HIFU).

BACKGROUND OF THE INVENTION

The use of ultrasound for imaging and diagnosis of disease is well known in the medical field. In therapeutic applications, absorbed ultrasound energy is used to change the state of a target area. In particular, ultrasound energy applied at high power densities can induce significant physiological effects on tissues. These effects may result from either thermal or mechanical response of the tissue subjected to ultrasound energy. Thermal effects include hyperthermia and ablation of tissue. The absorption of ultrasound energy at the target area induces a sudden temperature rise, which causes coagulation or ablation of target area cells.

In therapeutic applications of ultrasound, it is important that the applied ultrasound energy causes an intended change of state solely at a target area without adversely affecting other tissue within the patient. The effective therapeutic dose must be delivered to the target area while the thermal and mechanical effects in intermediary and surrounding tissue are minimized. Therefore, proper focusing and control of HIFU is one of the primary criteria for successful therapeutic application of ultrasound.

As described in U.S. Pat. No. 6,007,499 to Martin et al. and U.S. Pat. No. 6,042,556 to Beach et al., which are incorporated herein by reference, in HIFU hyperthermia treatments, the intensity of ultrasonic waves generated by a focused transducer increases from the source to the region of focus, where it can reach a very high temperature. The absorption of the ultrasonic energy at the focal region induces a sudden temperature rise of affected tissue that causes the irreversible ablation of the target volume of cells. HIFU hyperthermia treatments may be intended, for example, to cause necrosis of an internal lesion without damage to intermediate tissues.

Methods have been developed to increase the intensity of HIFU used for therapeutic purposes. For example, U.S. Pat. No. 5,092,336 to Fink, which is incorporated herein by reference, describes a device for localization and focusing of acoustic waves in tissues. The invention is based upon a technique known as time-reversed acoustics, which is described in an article by Fink, entitled, "Time-reversed acoustics," *Scientific American*, November 1999, pp. 91–97, which is also incorporated herein by reference. Essentially, a target is enclosed by an array of transducers that delivers an unfocused acoustic beam on a reflective target in a medium, for example, a site in organic tissue. Reflected signals from the target detected by ultrasound transducers in a regular array outside the patient are stored, the distribution in time and the shapes of the echo signals are time-reversed, and the reversed signals are applied to the respective transducers of the array. In most cases, the target constitutes a secondary source, which reflects or scatters a wave beam applied to it.

U.S. Pat. No. 6,161,434 to Fink et al., which is incorporated herein by reference, describes methods to use time-reversed acoustics to search for a faint sound source. U.S. Pat. No. 5,428,999 to Fink, which is also incorporated herein by reference, describes methods for detecting and locating reflecting targets, ultrasound echographic imaging, and concentrating acoustic energy on a target.

One of the areas where ablation of tissue has proven to be an effective therapeutic technique is the treatment of cardiac arrhythmia, particularly atrial fibrillation. Cardiac arrhythmia occurs when regions of cardiac tissue abnormally conduct electric signals to adjacent tissue, thus disrupting the normal cycle and causing asynchronous rhythm. It has been found that primary sources of undesired signals are located in the tissue region along the pulmonary veins of the left atrium and in the superior pulmonary veins. After unwanted contractions are generated in the pulmonary veins or conducted through the pulmonary veins from other sources, they are conducted into the left atrium where they can initiate or continue atrial fibrillation. By selective ablation of cardiac tissue, it is possible to cease or modify the propagation of unwanted electrical signals from one portion of the heart to another. The ablation process essentially destroys the unwanted electrical pathways by formation of non-conducting lesions.

Various means for performing ablation of cardiac tissue in the prior art include injection of a chemical such as ethanol into specific regions of the heart, or application of cryoablation, RF electrical current, microwave energy, lasers, and ultrasonic energy.

U.S. Pat. No. 5,807,395 to Mulier et al., and U.S. Pat. No. 6,190,382 to Ormsby et al., which are incorporated herein by reference, describe systems for ablating body tissue using radio frequency. U.S. Pat. Nos. 6,251,109 and 6,090,084 to Hassett et al., U.S. Pat. No. 6,117,101 to Diederich et al., U.S. Pat. Nos. 5,938,660 and 6,235,025 to Swartz et al., U.S. Pat. Nos. 6,245,064 and 6,024,740 to Lesh et al., U.S. Pat. Nos. 6,012,457, 6,164,283, 6,305,378 and 5,971,983 to Lesh, U.S. Pat. No. 6,004,269 to Crowley et al., and U.S. Pat. No. 6,064,902 to Haissaguerre et al., which are incorporated herein by reference, describe apparatus for tissue ablation to treat atrial arrhythmia, primarily by ablating tissue located within the pulmonary veins or on the ostia of the pulmonary veins.

HIFU has been used to ablate tissue within a beating heart. An article entitled "Extracardiac ablation of the canine atrioventricular junction by use of high-intensity focused ultrasound," by S A Strickberger et al., *Circulation*, 100, 203–208 (1999), which is incorporated herein by reference, describes the experimental use of HIFU to ablate the atrioventricular junction within a beating heart.

PCT Patent Publication WO 97/29699 to Ben-Haim, entitled, "Intrabody energy focusing," which is assigned to the assignee of the present patent application and is incorporated herein by reference, describes methods for optimizing irradiation of a target area of the body by using a radiation-sensing probe inserted into the body.

U.S. Pat. No. 5,590,657 to Cain et al., which is incorporated herein by reference, describes a HIFU system including a phased array of ultrasound transducers located outside the patient. Methods for refocusing the beam are described.

U.S. Pat. No. 6,128,958 to Cain, which is incorporated herein by reference, describes an architecture for driving an ultrasound phased array.

U.S. Pat. No. 5,769,790 to Watkins et al., which is incorporated herein by reference, describes a system for combining ultrasound therapy and imaging.

U.S. Pat. No. 5,762,066 to Law et al., which is incorporated herein by reference, describes a HIFU system consisting of an intracavity probe having two active ultrasound radiating surfaces with different focal geometries.

U.S. Pat. No. 5,366,490 to Edwards et al., which is incorporated herein by reference, describes a method for applying destructive energy to a target tissue using a catheter.

U.S. Pat. Nos. 5,207,214 and 5,613,940 to Romano, which are incorporated herein by reference, describe an array of reciprocal transducers which are intended to focus intense sound energy without causing extraneous tissue damage.

U.S. Pat. No. 5,241,962 to Iwama, which is incorporated herein by reference, describes the use of ultrasonic pulses and echo signals to disintegrate a calculus.

An article entitled, "High intensity focused ultrasound effect on cardiac tissues: Potential for clinical application," by L A Lee et al., *Echocardiography*, 17(6 Pt 1), 563–566 (2000), which is incorporated herein by reference, describes the use of HIFU to create lesions in mammalian cardiac tissues ex vivo.

An article entitled, "High intensity focused ultrasound phased arrays for thermal ablation of myocardium," by J U Kluiwstra et al., University of Michigan Medical Center, Department of Internal Medicine (undated), which is incorporated herein by reference, describes the experimental use of a combined ultrasound imaging and therapy system to place lesions at various locations in the heart under real-time ultrasound image guidance.

The following references, which are incorporated herein by reference, may be useful:

Hill C R et al., "Review article: High intensity focused ultrasound-potential for cancer treatment," *Br J Radiol*, 68(816), 1296–1303 (1995)

Lin W L et al., "A theoretical study of cylindrical ultrasound transducers for intracavitary hyperthermia," *Int J Radiat Oncol Biol Phys*, 46(5), 1329–36 (2000)

Chapelon J Y et al., "New piezoelectric transducers for therapeutic ultrasound," *Ultrasound Med Biol*, 26(1), 153–159 (2000)

Chauhan S et al., "A multiple focused probe approach for high intensity focused ultrasound based surgery," *Ultrasonics*, 39(1), 33–44 (2001)

Sommer F G et al., "Tissue ablation using an acoustic waveguide for high-intensity focused ultrasound," *Med Phys*, 24(4), 537–538 (1997)

Kluiwstra J U A et al., "Ultrasound phased arrays for noninvasive myocardial ablation: initial studies," *IEEE Ultrasonics Symposium Proceedings*, Vol. 2, 1604–1608 (1995)

Before performing ablation of cardiac tissue, it is often desirable to construct a map of the cardiac area of interest. Cardiac mapping is used to locate aberrant electrical pathways and currents within the heart, as well as to diagnose mechanical and other aspects of cardiac activity. Various methods and devices have been described for mapping the heart.

U.S. Pat. Nos. 5,546,951 and 6,066,094 to Ben-Haim, and European Patent 0 776 176 to Ben-Haim et al., which are assigned to the assignee of the present patent application and are incorporated herein by reference, describe methods for sensing an electrical property of heart tissue, for example, local activation time, as a function of the precise location within the heart. The data are acquired with a catheter that has electrical and location sensors in its distal tip, and which is advanced into the heart. Techniques for sensing cardiac electrical activity are also described in U.S. Pat. No. 5,471,982 to Edwards et al., commonly-assigned U.S. Pat. Nos. 5,391,199 and 6,066,094 to Ben-Haim, U.S. Pat. No. 6,052,618 to Dahlke et al., and in PCT patent publications WO94/06349 and WO97/24981, which are incorporated herein by reference.

Methods of creating a map of the electrical activity of the heart based on these data are described in U.S. Pat. Nos. 6,226,542 and 6,301,496 to Reisfeld, which are assigned to the assignee of the present patent application and are incorporated herein by reference. As indicated in these patents, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, which alters the propagation of the heart's electrical activity and restores normal heart rhythm. Methods for constructing a cardiac map of the heart are also described in U.S. Pat. Nos. 5,391,199 and 6,285,898 to Ben-Haim, and in U.S. Pat. Nos. 6,368,285 and 6,385,476 to Osadchy et al., which are assigned to the assignee of the present patent application and are incorporated herein by reference.

Catheters containing position sensors may be used to determine the trajectory of points on the cardiac surface. These trajectories may be used to infer motion characteristics such as the contractility of the tissue. As described in U.S. Pat. No. 5,738,096 to Ben-Haim, which is assigned to the assignee of the present application and which is incorporated herein by reference, maps depicting such motion characteristics may be constructed when the trajectory information is sampled at a sufficient number of points in the heart.

European Patent Application EP 1 125 549 and corresponding U.S. patent application Ser. No. 09/506,766 to Ben-Haim et al., which are assigned to the assignee of the present patent application and are incorporated herein by reference, describe techniques for rapidly generating an electrical map of a chamber of the heart. The catheter used for these techniques is described as comprising a contact electrode at the distal tip of the catheter and an array of non-contact electrodes on the shaft of the catheter near the distal end. The catheter also comprises at least one position sensor. Information from the non-contact electrodes and contact electrode is used for generating a geometric and electrical map of the cardiac chamber.

U.S. Pat. No. 5,848,972 to Triedman et al., which is incorporated herein by reference, describes a method for endocardial activation mapping using a multi-electrode catheter. A multi-electrode catheter is advanced into a chamber of the heart. Anteroposterior (AP) and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG. After the initial electrograms are recorded, the catheter is repositioned, and fluorograms and electrograms are once again recorded. An electrical map is then constructed from the above information.

U.S. Pat. No. 4,649,924 to Taccardi, which is incorporated herein by reference, describes a method for the detection of intracardiac electrical potential fields. The '924 patent is illustrative of non-contact methods that have been proposed to simultaneously acquire a large amount of cardiac electrical information. In the method of the '924 patent, a catheter having a distal end portion is provided with a series of sensor electrodes distributed over its surface and connected to insulated electrical conductors for connection to signal sensing and processing means. The size and shape of the end portion are such that the electrodes are spaced substantially away from the wall of the cardiac chamber. The method of the '924 patent is said to detect the intracardiac potential fields in only a single cardiac beat. The sensor electrodes are preferably distributed on a series of circumferences lying in planes spaced from each other. These planes are perpendicular to the major axis of the end portion of the catheter. At least two additional electrodes are provided adjacent the ends of the major axis of the end portion. The '924 patent describes a single exemplary embodiment in which the catheter comprises four circumferences with eight electrodes spaced equiangularly on each circumference. Thus, in that exemplary embodiment, the catheter comprises at least 34 electrodes (32 circumferential and 2 end electrodes).

PCT application WO 99/06112 to Rudy, which is incorporated herein by reference, describes an electrophysiological cardiac mapping system and method based on a non-contact, non-expanded multi-electrode catheter. Electrograms are obtained with catheters having from 42 to 122 electrodes. The relative geometry of the probe and the endocardium must be obtained via an independent imaging modality such as transesophageal echocardiography. After the independent imaging, non-contact electrodes are used to measure cardiac surface potentials and construct maps therefrom.

U.S. Pat. No. 5,297,549 to Beatty et al., which is incorporated herein by reference, describes a method and apparatus for mapping the electrical potential distribution of a heart chamber. An intra-cardiac multielectrode mapping catheter assembly is inserted into the heart. The mapping catheter assembly includes a multi-electrode array with an integral reference electrode, or, preferably, a companion reference catheter. In use, the electrodes are deployed in the form of a substantially spherical array. The electrode array is spatially referenced to a point on the endocardial surface by the reference electrode or by the reference catheter, which is brought into contact with the endocardial surface. Knowledge of the location of each of the electrode sites on the array, as well as a knowledge of the cardiac geometry is determined by impedance plethysmography.

U.S. Pat. No. 5,311,866 to Kagan et al., which is incorporated herein by reference, describes a heart mapping catheter assembly including an electrode array defining a number of electrode sites. The mapping catheter assembly has a lumen to accept a reference catheter having a distal tip electrode assembly which may be used to probe the heart wall. In the preferred construction, the mapping catheter includes a braid of insulated wires, preferably having 24 to 64 wires in the braid, each of which are used to form electrode sites. The catheter is said to be readily positionable in the heart to be used to acquire electrical activity information from a first set of non-contact electrode sites and/or a second set of in-contact electrode sites.

U.S. Pat. Nos. 5,385,146 and 5,450,846 to Goldreyer, which are incorporated herein by reference, describe a catheter that is said to be useful for mapping electrophysiological activity within the heart. The catheter body has a distal tip which is adapted for delivery of a stimulating pulse for pacing the heart or for ablating tissue in contact with the tip. The catheter further comprises at least one pair of orthogonal electrodes to generate a difference signal indicative of the local cardiac electrical activity adjacent the orthogonal electrodes.

U.S. Pat. No. 5,662,108 to Budd et al., which is incorporated herein by reference, describes a process for measuring electrophysiological data in a heart chamber. The method involves, in part, positioning a set of active and passive electrodes in the heart; supplying current to the active electrodes, thereby generating an electric field in the heart chamber; and measuring this electric field at the passive electrode sites. In one of the described embodiments, the passive electrodes are contained in an array positioned on an inflatable balloon of a balloon catheter.

SUMMARY OF THE INVENTION

It is an object of some aspects of the present invention to provide improved apparatus and methods for performing therapeutic procedures using high-intensity focused ultrasound (HIFU).

It is also an object of some aspects of the present invention to provide improved apparatus and methods for treatment of cardiac arrhythmia, particularly atrial fibrillation.

It is a further object of some aspects of the present invention to provide improved apparatus and methods that increase the accuracy of procedures for cardiac tissue ablation using HIFU.

It is yet a further object of some aspects of the present invention to provide apparatus and methods that increase the efficiency of procedures for cardiac tissue ablation using HIFU.

It is still a further object of some aspects of the present invention to provide apparatus and methods that increase the effectiveness of procedures using HIFU.

It is an additional object of some aspects of the present invention to provide apparatus and methods that reduce the risk of procedures using HIFU.

It is yet an additional object of some aspects of the present invention to provide apparatus and methods that reduce the trauma induced by some invasive procedures used to ablate cardiac tissue.

It is still an additional object of some aspects of the present invention to provide apparatus and methods to form ablation lesions in cardiac tissue.

It is also an object of some aspects of the present invention to provide apparatus and methods to achieve segmental conduction isolation in a pulmonary vein by use of HIFU.

It is a further object of some aspects of the present invention to provide apparatus and methods to achieve circumferential electrical conduction isolation in a pulmonary vein by use of HIFU.

In preferred embodiments of the present invention, apparatus for performing cardiac tissue ablation using HIFU comprises a catheter placed at a cardiac site of a patient, preferably within or at the ostium of a pulmonary vein or within a pulmonary vein in the vicinity of tissue to be ablated. The catheter comprises a beacon, preferably affixed to the distal end thereof, and, further preferably, a sensor for determination of the location of the beacon. An array of transducers located outside the patient's heart, typically on the skin, detects respective beacon signals comprising ultrasound energy from the beacon, and delivers electrical signals to a control unit, responsive to the detected energy. The control unit stores the shapes and distributions in time of the signals. Using techniques of time-reversed acoustics, the control unit reverses the distributions in time and the shapes of the signals and drives each transducer in the array to output its respective reversed signal, such that the generated waveform is accurately focused on the site of the beacon or in a vicinity thereof. The time-reversed waveforms are typically amplified, thus enabling a substantial amount of energy to be received within a short period at the target tissue location in the vicinity of the beacon.

The absorption of this energy in a short period causes ablation of the target tissue and formation of non-conducting lesions. Typically, the beacon is moved during the procedure so as to be in contact with a number of target sites, such that the lesions form one or more circumferential conduction blocks around the pulmonary vein, or a conduction block on a portion of the pulmonary vein. In some instances, the circumferential conduction block is formed in a manner such as to intersect with a similar circumferential conduction block around an adjacent pulmonary vein.

Typically, various combinations of conduction blocks are formed to treat the particular arrhythmia exhibited by the heart. For example, if the arrhythmia originates from a location in a pulmonary vein, a circumferential conduction block is formed along a path of the wall tissue that either includes the arrhythmogenic origin, thereby eliminating the source, or the block is formed between the origin and the left atrium, thereby preventing conduction of unwanted signals.

In some preferred embodiments of the present invention, the beacon actively emits ultrasound energy, preferably omnidirectional ultrasound energy, and the emitted energy is detected by the transducers of the array. Alternatively, the beacon comprises a passive ultrasound reflector. In this case, the beacon is preferably illuminated by an ultrasound beam, generated by some or all of the transducers of the array or by another source external to the body, and the array of transducers subsequently detects the echo of the beam. The beacon preferably is of a known geometry that produces a sharp and distinguishable signature that can be identified by the transducers or the control unit. Alternatively or additionally, the beacon is characterized by substantially higher reflectivity than the natural reflectivity of the surrounding tissue. Further alternatively, the beacon comprises a crystal with a predefined resonance frequency and a high Q, whereby the beacon is detected by the transducers when they generate the ultrasound beam at the resonance frequency. Still further alternatively, the beacon comprises a bubble containing an ultrasound contrast agent that reflects a known harmonic of the applied ultrasound beam. In this case, the transducers or control unit identifies the beacon by detecting the known harmonic of the applied frequency.

Thus, "beacon," as used in the context of the present patent application and in the claims, is to be understood as being indicative of both active and passive elements that respectively emit or reflect ultrasound energy.

In order to identify a desired site to be ablated, preferably, but not necessarily, a cardiac map is constructed prior to ablation. Methods and apparatus described hereinabove in the Background section are preferably but not necessarily used for constructing such a cardiac map. To assist in placing the beacon at the desired site, methods and apparatus are preferably but not necessarily utilized which are described in co-pending U.S. patent application Ser. No. 10/029,473, entitled, "Wireless Position Sensor," filed Dec. 21, 2001, and/or in co-pending U.S. patent application Ser. No. 10/029,595, entitled, "Implantable And Insertable Tags," filed Dec. 21, 2001. These applications are assigned to the assignee of the present patent application and are incorporated herein by reference. Alternatively or additionally, methods and apparatus known in the art are used to facilitate the placement of the beacon at a desired site in the heart.

In some embodiments in which the beacon comprises an active beacon, the control unit is coupled to the active beacon by leads, typically through the catheter. An electrical signal is sent to the active beacon, and the active beacon transduces the energy into the transmitted ultrasound energy, which is received by the transducers outside the patient's body. Alternatively, the active beacon comprises circuitry which wirelessly receives energy radiated from a remote site, typically located outside the patient's body, and the active beacon transduces the energy into the outputted ultrasound energy. Preferably, the energy received from the remote site comprises ultrasound energy and/or electromagnetic energy.

In accordance with these preferred embodiments of the present invention, application of HIFU from transducers located outside the body advantageously allows the use of a smaller catheter, because ablating hardware does not need to be included in the catheter. Additionally, the increased accuracy provided by these embodiments of the present invention typically increases the efficiency and/or effectiveness of procedures and reduces the likelihood of damage to untargeted surrounding tissue caused by HIFU waves.

Advantageously, the placement of the beacon enables HIFU to be accurately focused on a moving target, such as on a site in the beating heart. The array of transducers can be adapted to refocus the HIFU at a rapid rate responsive to the ultrasound energy from the moving beacon. Thus, whereas in prior art HIFU systems a relatively substantial amount of data must be recorded in order to have sufficient confidence that the moving tissue target site is accurately distinguished from surrounding non-target tissue, the use of an easily-distinguished or active beacon as provided by these embodiments of the present invention typically enables a smaller amount of data to be recorded in order to facilitate accurate HIFU application.

Additionally, the use of a beacon positioned at the target site raises the accuracy of HIFU ablation procedures by increasing the probability that the HIFU waves are focused on the precise location of the targeted tissue, and, additionally, that each external transducer is focused on generally the same location of the target. This is in contrast to other methods, which attempt to focus the HIFU waves on tissue having particular reflective or absorptive characteristics.

"Cardiac," as used in the present patent application and in the claims, is to be understood to mean "of or relating to the heart and/or the pulmonary veins."

There is therefore provided, in accordance with an embodiment of the present invention, apparatus for performing ablation of cardiac tissue using ultrasound, including:

a beacon, adapted to be placed at a cardiac site in a body of a subject; and a set of ultrasound transducers, each transducer adapted to detect a respective ultrasound signal coming from the beacon, and adapted to output a time-reversed ultrasound signal, reversed in time with respect to a property of at least one of the beacon signals, and configured to ablate the cardiac tissue.

The set of transducers is typically adapted to be applied to an external surface of the body of the subject.

In an embodiment, each transducer is adapted to configure its time-reversed signal to be reversed in time and shape with respect to a property of the beacon signal detected by that transducer.

Each transducer is typically adapted to amplify the time-reversed signal prior to outputting the time-reversed signal.

For some applications, the beacon is adapted to be placed at the cardiac site using a cardiac map of at least a portion of a heart of the subject.

For some applications, the one or more transducers include a single ultrasound transducer, and the single ultrasound transducer is adapted to output the time-reversed signal reversed in time with respect to a shape of the beacon signal detected by the single ultrasound transducer. For other applications, the one or more transducers include a plurality of transducers, each adapted to output the time-reversed signal reversed in time with respect to a sequence of detecting the beacon signal at the plurality of transducers.

In an embodiment, each transducer is adapted to regulate a timing parameter of the outputting of the respective time-reversed signal, responsive to a position of the transducer, a position of the beacon, and a position of the cardiac tissue.

For some applications, the apparatus includes a catheter having a distal end, which is adapted to be inserted into the body and brought to the cardiac site, wherein the beacon is adapted to be affixed in a vicinity of the distal end of the catheter.

Typically, the transducers are adapted to configure the respective time-reversed ultrasound signals to form one or more non-conducting lesions in the cardiac tissue.

For some applications, the cardiac tissue includes tissue that generates undesired electrical signals, and the transducers are adapted to configure the respective time-reversed ultrasound signals to be such as to form the one or more non-conducting lesions in the cardiac tissue. Alternatively, the cardiac tissue includes tissue through which propagate undesired electrical signals initially generated at a site outside of the cardiac tissue, and the transducers are adapted to configure the respective time-reversed ultrasound signals to be such as to form the one or more non-conducting lesions in the cardiac tissue.

In an embodiment, the beacon is adapted to be placed in a vicinity of a pulmonary vein of the subject. For example, the beacon may be adapted to be placed in a vicinity of an ostium of the pulmonary vein.

For some applications:
the beacon includes a passive element,
the apparatus includes an ultrasound transmitter, adapted to illuminate the beacon with an illuminating ultrasound signal, and
each transducer is adapted to detect an echo signal coming from the beacon responsive to illumination by the illuminating signal, and to output the time-reversed signal, reversed in time with respect to a property of the echo signal detected by that transducer.

In this case, in an embodiment of the present invention, the transmitter includes one of the transducers.

Alternatively or additionally, the passive element includes an ultrasound reflector, characterized by higher ultrasound reflectivity than a natural level of ultrasound reflectivity at the cardiac site. Further alternatively or additionally, the passive element is of a geometry that produces a distinguishable signature in the echo signal when the element is illuminated by the transmitter, and one or more of the transducers are adapted to detect the signature in the echo signal and to output the time-reversed signal responsive thereto. Still further alternatively or additionally, the passive element includes a crystal having a predefined resonance frequency. Yet further alternatively or additionally, the passive element includes an ultrasound contrast agent that reflects a known harmonic of the illuminating signal, and one or more of the transducers are adapted to detect the known harmonic and to output the time-reversed signal responsive thereto.

For some applications, the apparatus includes a control unit, adapted to store the beacon signals received from the beacon by each transducer, and adapted to drive each transducer to output its respective time-reversed signal. In this case, in an embodiment, each transducer is adapted to transform the beacon signals it receives into electrical signals, and to transmit the electrical signals to the control unit. Alternatively or additionally, the control unit is adapted to drive each transducer to configure its respective time-reversed signal to have a greater amplitude than a corresponding amplitude of the beacon signal received by the respective transducer.

In an embodiment, the beacon includes circuitry to receive energy, and wherein the beacon is adapted to transduce the received energy so as to generate the beacon signal. For example, the beacon may be adapted to configure the beacon signal to include one or more generally omnidirectional pulses.

Alternatively or additionally, the apparatus includes:
external power circuitry; and
a set of one or more wires connecting the external power circuitry to the beacon,
wherein the external power circuitry is adapted to transmit the energy to the beacon through the wires.

Alternatively, the circuitry is adapted to receive the energy wirelessly. For example, the apparatus may include a power transmitter, adapted to be located outside the body, and to wirelessly transmit the energy to the beacon. In this case, the power transmitter may be adapted to wirelessly transmit ultrasound energy and/or electromagnetic energy to the beacon.

In an embodiment of the present invention, the beacon is adapted to be placed in sequence at a plurality of locations in a vicinity of the cardiac site. For some applications, such locations include at least four non-coplanar locations. In an embodiment, each transducer is adapted to detect a respective beacon signal when the beacon is at each respective location, and to subsequently output the time-reversed signal, responsive to the respective beacon signals from the beacon at each respective location and responsive to a position of the cardiac tissue. For some applications, the beacon includes a location sensor, adapted to generate a respective location signal responsive to a respective location of the beacon, and each transducer is adapted to output the time-reversed signal responsive to the location signals. Alternatively or additionally, the one or more transducers include a plurality of ultrasound transducers, adapted to output the time-reversed signals responsive to the position of the cardiac tissue and reversed in time with respect to a sequence of detecting, at the plurality of transducers, the beacon signal when the beacon is at each location. For some applications, each transducer is adapted to regulate a timing parameter of the outputting of the time-reversed signal, responsive to a position of the transducer, a position of the beacon when the beacon is at each location, and the position of the cardiac tissue.

There is also provided, in accordance with an embodiment of the present invention, a method for performing ablation of cardiac tissue using ultrasound, including:

detecting, at one or more detection locations, respective beacon signals coming from a beacon placed at a cardiac site in a body of a subject;

reversing each of the beacon signals with respect to a time-based property thereof, to obtain respective time-reversed ultrasound signals; and generating the respective time-reversed ultrasound signals at each of the one or more locations, at a level sufficient to ablate the cardiac tissue.

In an embodiment, detecting at the one or more detection locations includes detecting at one or more locations on an external surface of the body of the subject.

In an embodiment, reversing each of the beacon signals includes reversing each of the beacon signals with respect to the time-based property thereof and a shape-based property thereof, to obtain the respective time-reversed signals.

Generating the time-reversed signals typically includes amplifying the time-reversed signals.

For some applications, detecting the respective beacon signals includes placing the beacon at the cardiac site using a cardiac map of at least a portion of a heart of the subject.

In accordance with an embodiment of the present invention, detecting the respective beacon signals at the one or more detection locations includes detecting a single beacon signal at a single detection location, and reversing each of the beacon signals includes reversing the single beacon signal with respect to the time-based property thereof.

In accordance with another embodiment, detecting the respective beacon signals at the one or more detection locations includes detecting a plurality of respective beacon signals at a plurality of respective detection locations, and reversing each of the beacon signals includes reversing each of the beacon signals with respect to a sequence of detecting, at the plurality of respective detection locations, the plurality of respective beacon signals.

For some applications, generating the time-reversed signals at each of the one or more detection locations includes regulating a timing parameter of generating the time-reversed signals at each of the one or more detection locations, responsive to a position of the respective detection location, a position of the beacon, and a position of the cardiac tissue.

In an embodiment, the beacon is affixed in a vicinity of a distal end of a catheter inserted into the body and brought to the cardiac site, and detecting the respective beacon signals includes detecting the respective beacon signals coming from the beacon when it is affixed to the catheter.

Alternatively or additionally, generating the time-reversed signals includes configuring the time-reversed signals to be such as to form one or more non-conducting lesions in the cardiac tissue. In this case, in an embodiment, the method includes identifying that the cardiac tissue generates undesired electrical signals. Alternatively, the method includes identifying that undesired electrical signals, initially generated at a site outside the cardiac tissue, propagate through the cardiac tissue.

In a typical embodiment, the cardiac site is in a vicinity of a pulmonary vein of the subject, and detecting the respective beacon signals includes detecting the respective beacon signals coming from the beacon when the beacon is in the vicinity of the pulmonary vein. For example, the cardiac site may be in a vicinity of an ostium of the pulmonary vein, and detecting the respective beacon signals includes detecting the respective beacon signals coming from the beacon when the beacon is in the vicinity of the ostium.

In an embodiment the beacon includes a passive beacon, and detecting the respective beacon signals includes illuminating the passive beacon with an illuminating ultrasound signal, and detecting respective ultrasound echo signals coming from the passive beacon, responsive to the illuminating. For example, the passive beacon may be characterized by higher ultrasound reflectivity than a natural level of ultrasound reflectivity at the cardiac site, and detecting the respective echo signals includes detecting the respective echo signals coming from the passive beacon, responsive to the higher ultrasound reflectivity. Alternatively or additionally, the passive beacon is of a geometry that produces a distinguishable signature in the echo signals when the beacon is illuminated with the illuminating signal, and detecting the respective echo signals includes detecting the signature in the respective echo signals. Further alternatively or additionally, the passive beacon includes a crystal having a predefined resonance frequency, illuminating the passive beacon includes illuminating with the illuminating signal at the resonance frequency, and detecting the respective echo signals includes detecting the respective echo signals coming from the passive beacon, responsive to illuminating with the illuminating signal at the resonance frequency. Still further alternatively or additionally, the passive beacon includes an ultrasound contrast agent that reflects a known harmonic of the illuminating signal, and detecting the respective echo signals includes detecting the known harmonic, responsive to illuminating with the illuminating signal.

In an embodiment, the method includes transducing, by the beacon, energy received by the beacon so as to generate the respective beacon signals. For example, the respective beacon signals may be characterized by one or more generally omnidirectional pulses, and transducing the received energy includes transducing the received energy so as to generate the generally omnidirectional pulses. As appropriate, the method includes transmitting the energy to the beacon through a set of one or more wires connected to the beacon. Alternatively or additionally, the method includes wirelessly transmitting the energy to the beacon. In this latter case, in an embodiment, the energy includes ultrasound energy, and wirelessly transmitting the energy includes wirelessly transmitting the ultrasound energy to the beacon. Alternatively or additionally, the energy includes electromagnetic energy, and wirelessly transmitting the energy includes wirelessly transmitting the electromagnetic energy to the beacon.

For some applications, detecting the respective beacon signals includes detecting each respective beacon signal when the beacon is placed in sequence at a plurality of respective beacon locations in a vicinity of the cardiac site. For example, detecting the respective beacon signals may include detecting the respective beacon signals when the beacon is placed in sequence at the plurality of beacon locations, such beacon locations including at least four non-coplanar beacon locations. Alternatively or additionally, detecting the respective beacon signals includes detecting each respective beacon signal when the beacon is at each respective beacon location, and generating the time-reversed signals includes subsequently generating the time-reversed signals, responsive to the respective beacon signals from the beacon at each beacon location and responsive to a position of the cardiac tissue. For example, generating the time-reversed signals may include generating the time-reversed signals responsive to a respective beacon position signal generated by the beacon at each respective beacon location. Alternatively or additionally, detecting the respective beacon signals at the one or more detection locations includes detecting a plurality of beacon signals at a respective plurality of detection locations, and reversing each of the beacon signals includes reversing each of the beacon signals responsive to the position of the cardiac tissue and with respect to a sequence of detecting, at the plurality of detection locations, the respective plurality of beacon signals.

For some applications, generating the time-reversed signals at each of the one or more detection locations includes regulating a timing parameter of the generation of the time-reversed signal, responsive to a position of each respective detection location, a position of the beacon when the beacon is at each beacon location, and the position of the cardiac tissue.

The present invention will be more fully understood from the following detailed description of the preferred embodiments thereof, taken together with the drawings, in which:

DETAILED DESCRIPTION OF PREFERRED EMBODIMENTS

Figure 1:
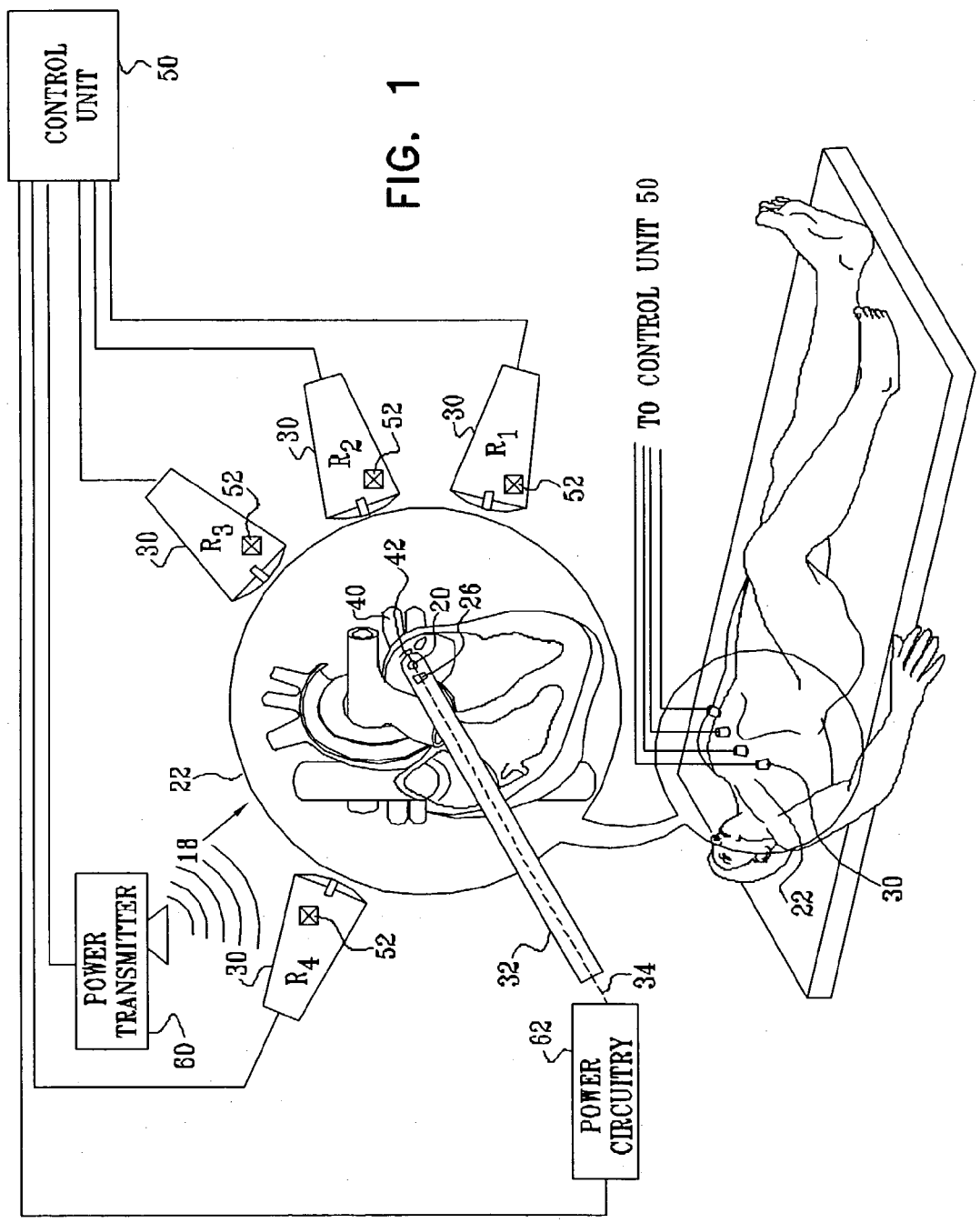
FIG. 1 is a simplified pictorial illustration showing a HIFU therapeutic system for application of energy to a cardiac site of a patient, in accordance with a preferred embodiment of the present invention.

FIG. 1 is a simplified pictorial illustration showing a HIFU tissue ablation system 18 applied to a cardiac site 42 of a patient, in accordance with a preferred embodiment of the present invention. HIFU ablation system 18 comprises a plurality of ultrasound transducers 30 which are coupled to a control unit 50. Transducers 30 are preferably applied in an array to the surface 22 of the patient's body such as the skin of the chest. The transducers may be of a design known in the art, and typically include piezoelectric elements. Transducers 30 detect ultrasound energy from a beacon 20, and deliver electrical signals, responsive thereto, to control unit 50.

Beacon 20 is typically mounted on the distal end of a guide tube 32, such as a catheter, and placed in close proximity to cardiac site 42 at which the intended ablation is to be performed. Typically, cardiac site 42 is within or at the ostium of a pulmonary vein 40. In order to identify a desired site to be ablated, preferably a cardiac map is constructed prior to ablation. Methods and apparatus for mapping described hereinabove in the Background section are preferably but not necessarily used for constructing such a cardiac map. To determine the location of beacon 20, a location sensor 26 is preferably positioned on guide tube 32, preferably in close proximity to beacon 20. Methods and apparatus are preferably utilized which are described in one or both of the above-cited US patent applications, entitled, "Wireless Position Sensor," and "Implantable And Insertable Tags," which are both incorporated herein by reference, or using radiofrequency or other position-sensing methods and apparatus known in the art. The location (position sensor) sensor 26 in one embodiment according to the present invention is an electromagnetic field responsive location sensor responsive to electromagnetic fields generated by magnetic field generators/radiators as part of a location system for determining the location, i.e. position and orientation of the location sensor 26. The location includes up to six directions and orientations such as (X, Y, Z directions and Pitch, Yaw and Roll orientations). The location system including the location sensor 26 and magnetic field generators (radiators) are described in greater detail in U.S. patent application Ser. No. 08/793,371 entitled "Medical Diagnosis, Treatment and Imaging Systems", filed May 14, 1997, the disclosure of which is incorporated herein by reference. Alternatively or additionally, the position of beacon 20 is determined using other methods (e.g., fluoroscopy).

For some applications, control unit 50 drives power circuitry 62 to transmit power to beacon 20 through power wires 34, which typically comprise leads passed through guide tube 32. Alternatively, control unit 50 drives a power transmitter 60, typically located outside the patient's body, to wirelessly transmit power to beacon 20, in which case beacon 20 comprises circuitry which receives the radiated energy. As appropriate, the energy radiated from power transmitter 60 includes ultrasound and/or electromagnetic energy. Alternatively, one or more of transducers 30 are adapted to wirelessly transmit power to beacon 20, preferably in the form of ultrasound energy; in this embodiment, power transmitter 60 is not used.

In accordance with a preferred embodiment of the present invention, beacon 20 transduces the received energy (whether received wirelessly or over power wires 34) into outputted ultrasound energy, typically as one or more omnidirectional pulses.

In an alternative embodiment, beacon 20 comprises a passive reflector that is illuminated (propagated) by an ultrasound beam, generated by a transmitter such as one or more of transducers 30, and transducers 30 detect the echo of the beam. In this embodiment, beacon 20 preferably is of a geometry that produces a sharp and distinguishable signature that can be identified by transducers 30 or control unit 50. Alternatively or additionally, beacon 20 is characterized by substantially higher reflectivity than the natural reflectivity of structure 40 and/or the surrounding tissue. Further alternatively, beacon 20 comprises a crystal with a predefined resonance frequency and a high Q so that beacon 20 is only detected by transducers 30 when they generate the ultrasound beam at a certain frequency. Still further alternatively, beacon 20 comprises a bubble containing an ultrasound contrast agent that reflects a known harmonic of the applied ultrasound beam. In this case, transducers 30 or control unit 50 identifies beacon 20 by detecting the known harmonic of the applied frequency.

The waveform from beacon 20 is detected by each of transducers 30, typically after a delay which is dependent upon (a) the distance between the beacon and each individual transducer 30 in the array, and (b) the transmission properties of the tissue through which the ultrasound energy passes prior to being received by each individual transducer 30. In addition to the delay, the shape of the waveform received at each individual transducer 30 is typically different from that received at other transducers because of the variation in absorption properties in the various intermediate tissues. The waveform received by transducers 30 is transformed into electrical signals and the shapes and relative positions in time of the signals are stored in control unit 50.

Figure 2B:
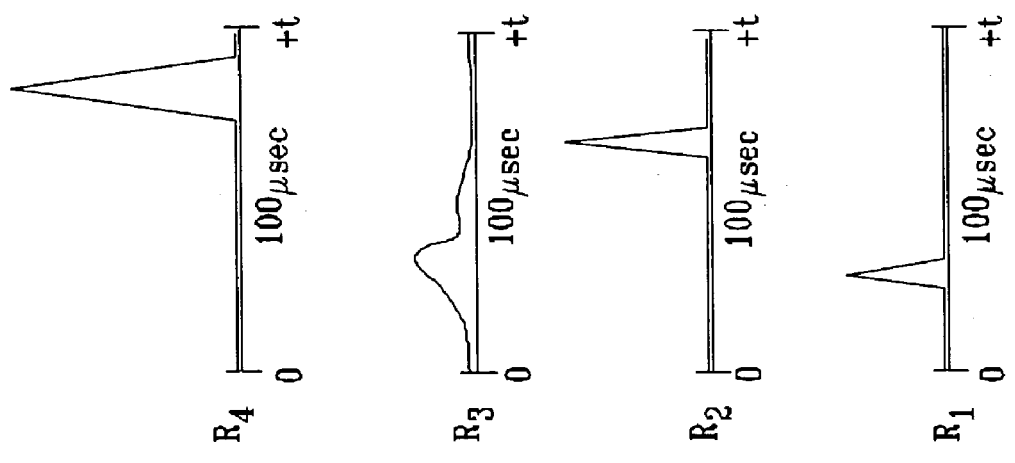
FIGS. 2A and 2B are timing diagrams showing one example of electrical signals respectively conveyed by the transducers to a control unit (FIG. 2A) and conveyed by the control unit to the transducers (FIG. 2B), in accordance with a preferred embodiment of the present invention.
Figure 2A:
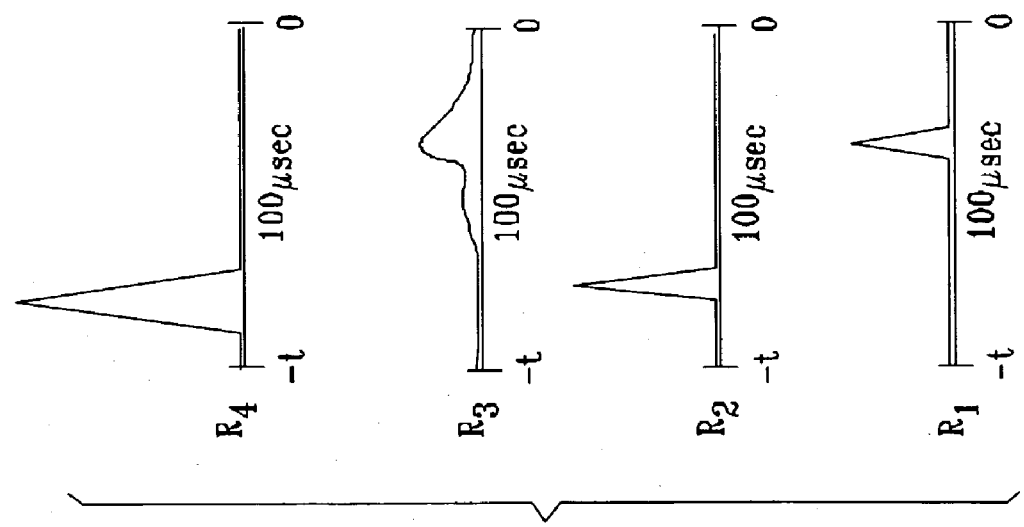

Reference is now made to FIGS. 2A and 2B. FIG. 2A is a timing diagram showing one example of electrical signals conveyed from transducers 30 to control unit 50, responsive to the ultrasound signals received by the transducers from beacon 20. For illustrative purposes, transducer $R_1$ is shown conveying a heavily-attenuated signal approximately 40 microseconds after transducer $R_4$ conveys a less attenuated signal. Transducers $R_2$ and $R_3$ are shown conveying signals of different delay and shape.

In accordance with a preferred embodiment of the present invention, upon receipt of the electrical signals from transducers 30, control unit 50 uses techniques of time-reversed acoustics (e.g., those described in the above-cited patents or article by Fink) to reverse the distributions in time and the shapes of the signals.

FIG. 2B is an example timing diagram showing reversed electrical signals generated by control unit 50, corresponding to the example signals shown in FIG. 2A, in accordance with a preferred embodiment of the present invention. For some applications, control unit 50 drives each of transducers 30 to output its respective reversed signal, such that the generated waveform is accurately focused on the site of beacon 20, with any distortions occurring during transmission through the tissue from beacon 20 to transducers 30 being compensated for by generally identical but time-reversed distortions on the return path. Typically, the time-reversed waveforms are amplified in order to deposit substantial quantities of energy in short time periods in the immediate vicinity of the beacon, thereby raising the temperature of the target tissue and causing ablation. The lesions caused by tissue ablation cause blockage of conduction.

For some applications, particularly when the precise shape of the generated waveforms is not expected to greatly affect the amount of heat deposited at the site of beacon 20, control unit 50 reverses the sequence of ultrasound signals received at transducers 30 in order to generate the sequence of time-reversed waveforms generated by the transducers. Thus, for example, if four transducers receive shaped pulses at respective times t=0, 20, 45, and 50 microseconds, then the control unit may be adapted to drive the respective transducers to output square pulses at times 150, 130, 105, and 100 microseconds. These pulses converge at the site of the beacon generally simultaneously, thus resulting in a significant deposit of energy at the site in a short time period.

In the example shown in FIG. 1, beacon 20 is typically placed in a pulmonary vein 40 or at an ostium of a pulmonary vein 40. Typically, if it is determined that cardiac arrhythmia, such as atrial fibrillation, originates from a site in a pulmonary vein 40, one or more circumferential or segmental lesions are formed in the tissue of the pulmonary vein which includes the arrhythmogenic source, thus preventing creation of unwanted electrical signals. Typically, beacon 20 is moved during the procedure so as to be in contact with a number of target sites, in order to form such lesions. In some instances, the circumferential conduction block is formed in a manner such as to intersect with a similar circumferential conduction block created around an adjacent pulmonary vein. Alternatively, the lesion does not include the source, but instead creates circumferential ablation of tissue between the source and the left atrium. In this instance, the abnormal signals may still be created, but further conduction of the aberrant signals to the atrial wall tissue is prevented by the conduction block formed in or near the pulmonary vein by the lesion. As appropriate, various shapes and combinations of conduction blocks can be formed to treat the particular arrhythmia exhibited by the heart.

In a preferred embodiment of the present invention, each ultrasound transducer 30 comprises a position sensor 52, which generates a position signal indicative of the position of the respective transducer, preferably in a manner similar to the generation of position-determining signals by location sensor 26, as described above. Alternatively, the positions of the ultrasound transducers are determined using other methods (e.g., by rigid attachment to a fixed frame). In either case, the positions of the ultrasound transducers are registered in the reference frame of location sensor 26 on catheter 32.

According to this embodiment, cardiac site 42 comprises a plurality of target locations for ablation, arranged, for example, as a circumferential conduction block as described above. Preferably the target locations are determined using a cardiac map, as described above. Beacon 20 is brought into the vicinity of the cardiac site, and the position of the beacon is determined using location sensor 26.

The waveform from beacon 20 is detected by each of transducers 30, whether beacon 20 is an active element or a passive reflector illuminated (propagated) by an ultrasound beam, as described above. Control unit 50 uses techniques of time-reversed acoustics, as described above, to reverse the distributions in time and the shapes of each of the signals received by each of the transducers from the beacon location. In order to focus the time-reversed waveforms generated by transducers 30 sequentially onto each target location of cardiac site 42 rather than the location of the beacon, control unit 50 calculates an appropriate transmission signal for each transducer by reversing the shape of the respective signals received from the beacon. The control unit also determines appropriate time offsets responsive to (a) the time at which each transducer received the signal from the beacon, relative to the times at which the other transducers received the signal, and (b) the positions of transducers with respect to the beacon and each target location.

For example, as shown illustratively in FIG. 1, transducer $R_1$, beacon 20, cardiac site 42, and transducer $R_4$ generally lie at respective points along a line, with cardiac site 42 closer to transducer $R_1$ than to transducer $R_4$. Preferably, in this example, for each target location, the time-reversed signal emitted by transducer $R_1$ is initiated at a time t+dt, after initiation of transmission of the time-reversed signal from transducer $R_4$, such that the time-reversed signals from transducers $R_1$ and $R_4$ will strike the target location at generally the same time. Preferably, dt is selected based on the relative locations of the transducers, beacon 20, and each target location, as well as the speed of sound in tissue. In this manner, the ultrasound energy emitted by each of the transducers is preferably focused on the target location. This calculation and ultrasound emission is repeated for each target location of cardiac site 42, until the desired ablation block has been achieved.

Optionally, beacon 20 is placed at a plurality of sites in the vicinity of cardiac site 42, and waveforms are detected by the transducers while the beacon is at the respective sites. In this case, the control unit typically uses the waveform from the site of beacon 20 closest to each target location in order to increase the accuracy of the calculated emission signals. Alternatively or additionally, the control unit records the waveforms detected by the transducers while the beacon is at the respective sites, and subsequently determines appropriate time offsets to apply to the time-reversed signal generated by each of the transducers, in order to focus the time-reversed signals on each target location. Typically, the time offsets are determined responsive to the position of each of the sites visited by the beacon, the position of each of the transducers, and the position of each respective target location.

Advantageously, because each transducer 30 outputs its respective calculated reversed signal (albeit after an appropriate time delay, as described above), any distortions occurring during transmission through the tissue from the vicinity of cardiac site 42 to transducers 30 are compensated for by generally identical but time-reversed distortions on the return path. Typically, such distortions are substantially similar for each target location of cardiac site 42, because the target locations are near each other and most such distortions are introduced in the tissue between the cardiac site and the transducers.

For some applications, particularly when the precise shape of the generated waveforms is not expected to greatly affect the amount of heat deposited at the target sites, control unit 50 uses only signal timing information received from beacon 20, and not signal shape information, as described hereinabove. For example, the control unit may be adapted to drive the transducers to output square pulses at the appropriate times, rather than shape-reversed signals at the appropriate times.

In accordance with a preferred embodiment of the present invention, each step described hereinabove is performed iteratively, as appropriate. For example, in some applications, control unit 50 varies the magnitude of the ultrasound energy coming from beacon 20 and/or transducers 30, responsive to various factors, measurements, and conditions during a procedure. Also, particularly in the embodiments wherein the beacon comprises a passive reflective beacon, the process of focusing the transducer-generated HIFU may be iterative (e.g., as described in the above-cited patents to Fink or Fink et al. or article by Fink all of which are incorporated by reference).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for performing ablation of cardiac tissue using ultrasound, comprising:
   a beacon, adapted to be placed at a cardiac site in a body of a subject;
   a location sensor adapted to be located in proximity to the beacon at the cardiac site in the body for determining up to six directions and orientations of the beacon; and
   a set of ultrasound transducers, each transducer adapted to detect a respective ultrasound signal coming from the beacon, and adapted to output a time-reversed ultrasound signal, reversed in time with respect to a property of at least one of the beacon signals, and configured to ablate the cardiac tissue in the vicinity of the beacon at the cardiac site.

2. Apparatus according to claim 1, wherein the set of transducers is adapted to be applied to an external surface of the body of the subject.

3. Apparatus according to claim 1, wherein each transducer is adapted to configure its time-reversed signal to be reversed in time and shape with respect to a property of the beacon signal detected by that transducer.

4. Apparatus according to claim 1, wherein each transducer is adapted to amplify the time-reversed signal prior to outputting the time-reversed signal.

5. Apparatus according to claim 1, wherein the beacon is adapted to be placed at the cardiac site using a cardiac map of at least a portion of a heart of the subject.

6. Apparatus according to claim 1, wherein the one or more transducers comprise a single ultrasound transducer, and wherein the single ultrasound transducer is adapted to output the time-reversed signal reversed in time with respect to a shape of the beacon signal detected by the single ultrasound transducer.

7. Apparatus according to claim 1, wherein the one or more transducers comprise a plurality of transducers, each adapted to output the time-reversed signal reversed in time with respect to a sequence of detecting the beacon signal at the plurality of transducers.

8. Apparatus according to claim 1, wherein each transducer is adapted to regulate a timing parameter of the outputting of the respective time-reversed signal, responsive to a position of the transducer, a position of the beacon, and a position of the cardiac tissue.

9. Apparatus according to claim 1, comprising a catheter having a distal end, which is adapted to be inserted into the body and brought to the cardiac site, wherein the beacon is adapted to be affixed in a vicinity of the distal end of the catheter.

10. Apparatus according to claim 1, wherein the transducers are adapted to configure the respective time-reversed ultrasound signals to form one or more non-conducting lesions in the cardiac tissue.

11. Apparatus according to claim 10, wherein the cardiac tissue includes tissue that generates undesired electrical signals, and wherein the transducers are adapted to configure the respective time-reversed ultrasound signals to be such as to form the one or more non-conducting lesions in the cardiac tissue.

12. Apparatus according to claim 10, wherein the cardiac tissue includes tissue through which propagate undesired electrical signals initially generated at a site outside of the cardiac tissue, and wherein the transducers are adapted to configure the respective time-reversed ultrasound signals to be such as to form the one or more non-conducting lesions in the cardiac tissue.

13. Apparatus according to claim 1, wherein the beacon is adapted to be placed in a vicinity of a pulmonary vein of the subject.

14. Apparatus according to claim 13, wherein the beacon is adapted to be placed in a vicinity of an ostium of the pulmonary vein.

15. Apparatus according to claim 1,
   wherein the beacon comprises a passive element, wherein the apparatus comprises an ultrasound transmitter, adapted to supply the beacon with a propagating ultrasound signal, and
   wherein each transducer is adapted to detect an echo signal coming from the beacon responsive to propagation by the propagating ultrasound signal, and to output the time-reversed signal, reversed in time with respect to a property of the echo signal detected by that transducer.

16. Apparatus according to claim 15, wherein the transmitter comprises one of the transducers.

17. Apparatus according to claim 15, wherein the passive element comprises an ultrasound reflector, characterized by higher ultrasound reflectivity than a natural level of ultrasound reflectivity at the cardiac site.

18. Apparatus according to claim 15, wherein the passive element is of a geometry that produces a distinguishable signature in the echo signal when the element is propagated by the transmitter, and wherein one or more of the transducers are adapted to detect the signature in the echo signal and to output the time-reversed signal responsive thereto.

19. Apparatus according to claim 15, wherein the passive element comprises a crystal having a predefined resonance frequency.

20. Apparatus according to claim 15, wherein the passive element comprises an ultrasound contrast agent that reflects a known harmonic of the propagating signal, and wherein one or more of the transducers are adapted to detect the known harmonic and to output the time-reversed signal responsive thereto.

21. Apparatus according to claim 1, comprising a control unit, adapted to store the beacon signals received from the beacon by each transducer, and adapted to drive each transducer to output its respective time-reversed signal.

22. Apparatus according to claim 21, wherein each transducer is adapted to transform the beacon signals it receives into electrical signals, and to transmit the electrical signals to the control unit.

23. Apparatus according to claim 21, wherein the control unit is adapted to drive each transducer to configure its respective time-reversed signal to have a greater amplitude than a corresponding amplitude of the beacon signal received by the respective transducer.

24. Apparatus according to claim 1, wherein the beacon comprises circuitry to receive energy, and wherein the beacon is adapted to transduce the received energy so as to generate the beacon signal.

25. Apparatus according to claim 24, wherein the beacon is adapted to configure the beacon signal to include one or more generally omnidirectional pulses.

26. Apparatus according to claim 24, comprising:
external power circuitry; and
a set of one or more wires connecting the external power circuitry to the beacon,
wherein the external power circuitry is adapted to transmit the energy to the beacon through the wires.

27. Apparatus according to claim 24, wherein the circuitry is adapted to receive the energy wirelessly.

28. Apparatus according to claim 27, comprising a power transmitter, adapted to be located outside the body, and to wirelessly transmit the energy to the beacon.

29. Apparatus according to claim 28, wherein the power transmitter is adapted to wirelessly transmit ultrasound energy to the beacon.

30. Apparatus according to claim 28, wherein the power transmitter is adapted to wirelessly transmit electromagnetic energy to the beacon.

31. Apparatus according to claim 1, wherein the beacon is adapted to be placed in sequence at a plurality of locations in a vicinity of the cardiac site.

32. Apparatus according to claim 31, wherein the beacon is adapted to be placed at the plurality of locations, such locations including at least four non-coplanar locations.

33. Apparatus according to claim 31, wherein each transducer is adapted to detect a respective beacon signal when the beacon is at each respective location, and to subsequently output the time-reversed signal, responsive to the respective beacon signals from the beacon at each respective location and responsive to a position of the cardiac tissue.

34. Apparatus according to claim 33, wherein the beacon comprises a location sensor, adapted to generate a respective location signal responsive to a respective location of the beacon, and wherein each transducer is adapted to output the time-reversed signal responsive to the location signals.

35. Apparatus according to claim 33, wherein the one or more transducers comprise a plurality of ultrasound transducers, adapted to output the time-reversed signals responsive to the position of the cardiac tissue and reversed in time with respect to a sequence of detecting, at the plurality of transducers, the beacon signal when the beacon is at each location.

36. Apparatus according to claim 33, wherein each transducer is adapted to regulate a timing parameter of the outputting of the time-reversed signal, responsive to a position of the transducer, a position of the beacon when the beacon is at each location, and the position of the cardiac tissue.

* * * * *